United States Patent
Boutenko et al.

(10) Patent No.: US 6,332,014 B1
(45) Date of Patent: Dec. 18, 2001

(54) METHOD OF IMPROVING THE QUALITY OF A FLUOROSCOPIC IMAGE

(75) Inventors: Vladislav Boutenko, Boulogne Billancourt; Bernard Callier, Voisins-le-Bretonneux; Huburt Hacquard, Bièvres; François Kotian, Bois d'Arcy, all of (FR)

(73) Assignee: GE Medical Systems S.A. (FR)

( * ) Notice: Subject to any disclaimer, the term of this patent is extended or adjusted under 35 U.S.C. 154(b) by 0 days.

(21) Appl. No.: 09/415,156

(22) Filed: Oct. 8, 1999

(30) Foreign Application Priority Data

Aug. 31, 1998 (FR) .................................................. 98 10876

(51) Int. Cl.⁷ ....................................................... A61B 6/00
(52) U.S. Cl. ................................................. 378/95; 378/42
(58) Field of Search ................................. 378/42, 62, 95, 378/98.2

(56) References Cited

U.S. PATENT DOCUMENTS

| | | | |
|---|---|---|---|
| 4,382,184 | * 5/1983 | Wernikoff | 378/37 |
| 4,433,428 | * 2/1984 | Haendle et al. | 378/95 |
| 4,611,340 | * 9/1986 | Okazaki | 378/95 |
| 4,680,628 | * 7/1987 | Wojcik et al. | 378/98.2 |
| 4,689,670 | * 8/1987 | Okazaki | 378/98.5 |
| 4,709,385 | * 11/1987 | Pfeiler et al. | 378/95 |
| 4,716,904 | * 1/1988 | Meno | 378/98.5 |
| 5,117,446 | * 5/1992 | Haaker et al. | 378/95 |
| 5,400,383 | 3/1995 | Yassa | 378/98.2 |
| 5,448,614 | 9/1995 | Suzuki | 378/115 |
| 5,546,440 | 8/1996 | Nakatani et al. | 378/98.2 |
| 5,832,051 | * 11/1998 | Lutz | 378/95 |
| 6,154,516 | * 11/2000 | Heuscher et al. | 378/15 |

FOREIGN PATENT DOCUMENTS 3040425 5/1982 (DE).
4124791 1/1993 (DE).
4210121 4/1993 (DE).

OTHER PUBLICATIONS

Patent Abstracts of Japan, pub. No. 60050900, May 20, 1985.

* cited by examiner

*Primary Examiner*—Drew Dunn
(74) *Attorney, Agent, or Firm*—Jay L. Chaskin

(57) ABSTRACT

A method for improving the quality of a fluoroscopic image where the image out of an image sequence of images which satisfies a predetermined minimum motion criterion is stored and this stored image is continuously displayed. The images may be acquired using a pulsed cardiac fluoroscope.

12 Claims, 1 Drawing Sheet

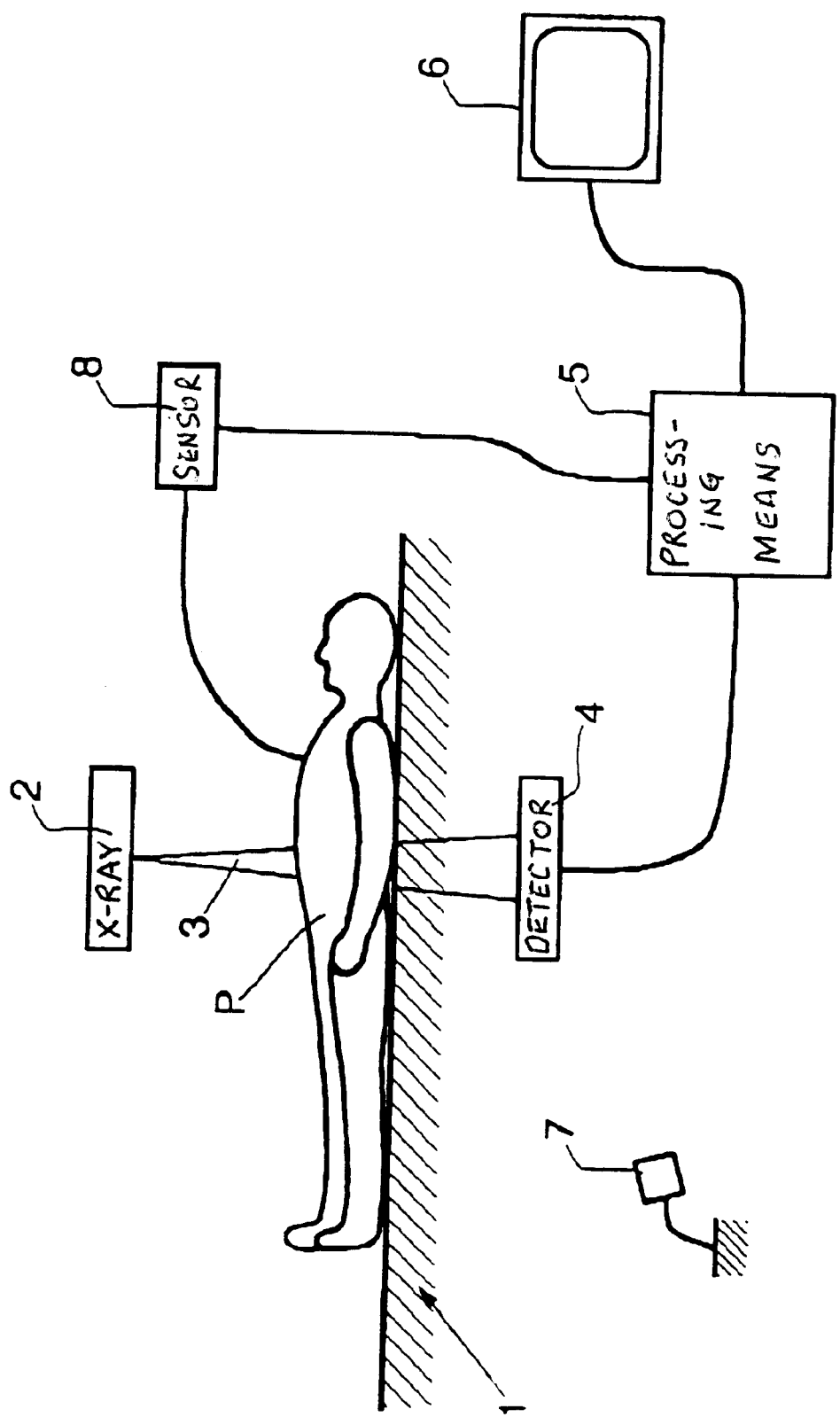

METHOD OF IMPROVING THE QUALITY OF A FLUOROSCOPIC IMAGE

BACKGROUND OF THE INVENTION

The invention relates to pulsed cardiac fluoroscopy and, more particularly, to improving the quality of a fluoroscopic image displayed continuously, that is to say, for example, when the operator takes his foot off the control pedal of the fluoroscopic image acquisition device.

Fluoroscopy consists in acquiring radiographic images (referred to below as fluoroscopic images) at a high rate, these being intended to be displayed a display screen. Fluoroscopy is, for display the path of probes injected directly on example, used into blood vessels.

There are several versions of fluoroscopy. In this regard, mention may be made of what is referred to as continuous fluoroscopy, characterized by continuous exposure of the patient to X-rays, and what is referred to as pulsed fluoroscopy, characterized by X-ray pulses which have a predetermined time width and are repeated at the frequency with which the pictures are taken.

Thus, in pulsed fluoroscopy, when the operator presses the control pedal of the device, X-ray pulses are emitted sequentially, each pulse making it possible to acquire one fluoroscopic image.

When the operator takes his foot off the pedal, a fluoroscopic image is then displayed continuously on the display screen, and this image needs to be as sharp as possible. However, the beating of the heart causes the patient's chest to move, which leads to blurring of the images displayed in cardiac fluoroscopy.

BRIEF SUMMARY OF THE INVENTION

An embodiment of the invention provides for continuous display of a fluoroscopic image with the best possible sharpness, while minimizing the stresses experienced by the X-ray tube so as not to shorten its life.

An embodiment of the invention therefore provides a method of improving the quality of a fluoroscopic image displayed continuously following an image acquisition sequence in which the images are acquired using pulsed cardiac fluoroscope, in which that image out of the sequence of images which satisfies a predetermined minimum motion criterion is stored and this stored image is continuously displayed.

BRIEF DESCRIPTION OF THE DRAWING

Other advantages and characteristics of the invention will become apparent on studying the detailed description of entirely non-limiting embodiments, and the appended drawing in which the single FIGURE very schematically represents a system for acquiring fluoroscopic images.

DETAILED DESCRIPTION OF THE INVENTION

In the single FIGURE reference 1 denotes a table supporting a patient P. An X-ray generator 2 emits X-ray pulses at regular time intervals when the acquisition pedal 7 of the device is depressed. When each pulse is emitted, an X-ray beam 3 passes through the patient and is received on a detector 4 connected to processing means 5 whose architecture is based on a microcomputer. The images which are acquired are displayed on a display screen 6.

According to a first embodiment of the invention, when the operator presses the pedal 7, X-ray pulses are successively emitted at predetermined time intervals with, for example, a pulse width of the order of 15 ms. The images which are acquired are displayed directly on the display screen 6 after having been processed by the processing means 5. When the operator takes his foot off the pedal 7, the processing means 5 supply the X-ray generator with a control signal whose effect is to reduce the length of the pulse emitted, from 15 ms to about 5 ms. Furthermore, since the X-ray dose per image must remain constant, the level of X-rays emitted on this last image is increased, which it possible to improve the sharpness of this image which is acquired and displayed continuously on the screen 6.

The person skilled in the art will therefore note that the increased heating of the X-ray tube due to the shortening of the pulse occurs only on the last image, and this does not therefore shorten the life of the tube.

According to another embodiment of the invention, the processing means 5 carry out image processing on the images of the sequence, so as to store the one which satisfies a minimum blur criterion. More specifically, for example, image-to-image correlation processing may be carried out on small areas of the image. Maximum correlation between two successive images is representative of minimum movement between these two images. The image associated with maximum correlation is then stored in real time.

This image processing may be carried out image by image, or alternatively on all the images of the 10 last cardiac cycle, which are continually stored.

According to another variant of the invention, a sensor 8 may be used, for example a blood pressure sensor or alternatively a device for electrocardiogram, so as to detect a diastole termination time, that is to say a time when the heart moves the least. The sensor then emits control signal to the processing means 5 which then store the image acquired at this time in a memory so as to display it continuously at the end of the acquisition of the image sequence, that is to say when the operator takes his foot of the pedal 7.

The image stored may be the last image of the sequence, that is to say the one acquired when the operator takes his foot off the control pedal of the device. In this alternative embodiment, the invention provides for increasing the level of X-rays emitted on this last image, then storing this image.

In this embodiment variant, increasing the level of the X-rays leads to a shorter pulse length for thus the last image. This increased stress which the tube experiences is thus limited at the time when the last image is acquired. This pulse length is for example reduced to 5 ms whereas it is kept at 15 ms throughout the rest of the acquisition sequence.

According to another variant of the invention, image processing is carried out on the images of the sequence so as to store the one which satisfies a minimum blur criterion. By way of indication, this image processing may consist in an image to image correlation over small regions. The maximum correlation between two successive images is then looked for.

According to another variant of the invention, a sensor, for example a blood pressure sensor or, alternatively, a device for recording an electrocardiogram, is used to detect a diastole to termination time corresponding to very little movement of the heart, and, in response to a control signal emitted by the sensor, the image acquired when this control signal is received is stored.

Various modifications in structure and/or function and/or steps may be made by one skilled in the art to the disclosed embodiment without departing from the scope and extent of the invention.

What is claimed is:

1. A method for improving the quality of a fluoroscopic image obtained by transmitting X-rays at a preselected level through an object with the image being displayed as a sequence of images, the method comprising the steps of:

processing the sequence of images to identify an image out of the sequence of images which satisfies a predetermined minimum motion criterion;

storing the identified image; and continuously displaying the stored image.

2. The method according to claim 1, wherein the level of X-rays emitted is increased from the preselected level on the last image of the sequence and this image is stored.

3. The method according to claim 1, wherein the processing of the images is carried out on the images of the sequence to store the image which satisfies a minimum blur criterion.

4. The method of claim 1, wherein a diastole termination time is detected, and, in response to this determination, the image is acquired and stored.

5. The method according to claim 1, wherein the images are acquired using a pulsed cardiac fluoroscope.

6. The method according to claim 1, wherein the sequence of images is obtained following an image acquisition sequence including the step of detecting a diastolic termination time.

7. The method according to claim 2 wherein the emitted X-rays have a pulse length for the last image which is less than the pulse length in a previous image of the sequence.

8. The method according to claim 1 wherein image processing is image to image correlation and determining the maximum correlation between two successive images.

9. A method of displaying a fluoroscopic image following an image acquisition sequence comprising the steps of:

sequentially transmitting X-rays through an object to be imaged;

detecting the X-rays after passing through the object;

acquiring a sequence of images of the object using a pulsed fluoroscope;

storing an image of the sequence of images which satisfies a predetermined minimum motion criterion; and continuously displaying the stored image.

10. The method according to claim 9 wherein the image stored is the last image in the sequence of images.

11. The method according to claim 9 wherein the image stored is the image which satisfies a minimum blur criterion.

12. The method according to claim 9 wherein the criterion is the determination of the time when the object has minimum movement.

* * * * *